United States Patent
Meskens et al.

(10) Patent No.: US 8,953,810 B2
(45) Date of Patent: Feb. 10, 2015

(54) SYNCHRONIZATION IN A BILATERAL AUDITORY PROSTHESIS SYSTEM

(75) Inventors: Werner Meskens, Opwijk (BE); Tony M. Nygard, Terrigal (AU)

(73) Assignee: Cochlear Limited, Macquarie University, NSW (AU)

( * ) Notice: Subject to any disclaimer, the term of this patent is extended or adjusted under 35 U.S.C. 154(b) by 806 days.

(21) Appl. No.: 13/040,150

(22) Filed: Mar. 3, 2011

(65) Prior Publication Data

US 2012/0224705 A1    Sep. 6, 2012

(51) Int. Cl.
*H04R 5/00* (2006.01)
*H04R 25/00* (2006.01)
*A61N 1/36* (2006.01)

(52) U.S. Cl.
CPC .......... *H04R 25/552* (2013.01); *A61N 1/36032* (2013.01); *H04R 2460/03* (2013.01)
USPC ........... 381/23.1; 381/312; 381/315; 381/316

(58) Field of Classification Search
USPC ................................. 381/23.1, 315, 312, 316
See application file for complete search history.

(56) References Cited

U.S. PATENT DOCUMENTS

| | | | |
|---|---|---|---|
| 4,918,736 A | 4/1990 | Bordewijk | |
| 6,694,034 B2 | 2/2004 | Julstrom et al. | |
| 6,768,802 B1 | 7/2004 | Baechler | |
| 6,978,181 B1 | 12/2005 | Snell | |
| 7,020,296 B2 | 3/2006 | Niederdrank | |
| 7,245,731 B2 | 7/2007 | Niederdrank et al. | |
| 7,447,325 B2 | 11/2008 | Bren et al. | |
| 7,580,534 B2 | 8/2009 | Fischer | |
| 7,702,121 B2 | 4/2010 | Husung et al. | |
| 2001/0051766 A1 | 12/2001 | Gazdzinski | |
| 2003/0119568 A1 | 6/2003 | Menard | |
| 2005/0089001 A1 | 4/2005 | Nishikawa | |
| 2005/0089183 A1 | 4/2005 | Niederdrank et al. | |
| 2007/0140506 A1 | 6/2007 | Roeck | |
| 2007/0147641 A1 | 6/2007 | Platz | |
| 2007/0249289 A1 | 10/2007 | Grafenberg et al. | |
| 2007/0253584 A1 | 11/2007 | Rass | |
| 2008/0049945 A1 | 2/2008 | Haenggi et al. | |

(Continued)

FOREIGN PATENT DOCUMENTS

| | | |
|---|---|---|
| DE | 20114461 | 7/2001 |
| EP | 1250026 | 10/2002 |

(Continued)

OTHER PUBLICATIONS

Gu et al. "Radio Triggered Wake-Up for Wireless Sensor Networks" Department of Computer Science, University of Virginia, Real Time Systems, Springer, vol. (29) No. 2-3. ISSN: 0922-6443, Mar. 2005, pp. 157-182. (14 pages).

(Continued)

*Primary Examiner* — Paul S Kim

(57) ABSTRACT

Aspect of the present invention are generally directed to synchronization between a first auditory prosthesis and a second auditory prosthesis of a bilateral auditory prosthesis system. In this system, a primary wireless communications channel, usable for synchronizing the first and second prostheses, may be disabled to, for example, conserve power. Then, upon detection of a trigger in sound received by one or more of the prostheses, the primary wireless communication channel is enabled and the prostheses synchronized using the primary wireless communication channel.

21 Claims, 8 Drawing Sheets

(56) References Cited

U.S. PATENT DOCUMENTS

| | | | |
|---|---|---|---|
| 2008/0253593 A1* | 10/2008 | Bramslow et al. | 381/312 |
| 2009/0030484 A1 | 1/2009 | Chambers | |
| 2009/0052707 A1 | 2/2009 | Hain | |
| 2010/0181844 A1 | 7/2010 | Karalis et al. | |
| 2012/0232616 A1 | 9/2012 | Van Baelen et al. | |

FOREIGN PATENT DOCUMENTS

| | | |
|---|---|---|
| EP | 2026406 | 2/2009 |
| WO | WO 03101536 | 6/2003 |
| WO | 2004012477 | 2/2004 |
| WO | WO 2004034738 | 4/2004 |
| WO | WO 2006122836 | 11/2006 |
| WO | 2012120481 | 9/2012 |

OTHER PUBLICATIONS

Van der Doorn et al. "A Prototype low-cost wakeup radio for the 868 MHz band" Int. J. Sensor Networks, vol. 5, No. 1, 2009 pp. 22-32.

Zarlink Semiconductor, Inc., http://www.zarlink.com/zarlink/zl70101-product-preview-apr2007.pdf, (2007).

International Search Report and Written Opinion for International Application No. PCT/IB2012/051130 mailed Oct. 25, 2012 (18 pages).

* cited by examiner

SYNCHRONIZATION IN A BILATERAL AUDITORY PROSTHESIS SYSTEM

BACKGROUND

1. Field of the Invention

The present invention relates generally to auditory prostheses, and more particularly to synchronization in a bilateral auditory prosthesis system.

2. Related Art

Auditory prostheses include any acoustic or electrical auditory prostheses, such as hearing aids, middle ear implants, cochlear implants, brain stem implants, auditory mid-brain implants and other devices that provide electrical and/or acoustic stimulation to a recipient to assist with hearing. Such prostheses receive or generate an electrical signal corresponding to sound. The electrical signal is typically obtained from a microphone that receives the sound and generates a corresponding electrical signal. For example, a conventional cochlear implant includes an external part containing a microphone, sound processor and a headpiece coil; and an implanted part that contains an implant coil, and a stimulator device coupled to an electrode array.

Sound is received at the microphone, which generates an electrical signal that is delivered to the sound processor as an input. The sound processor processes the input signal and generates control signals, according to pre-defined sound processing strategy, for controlling the stimulation of the electrode array of the stimulator device. The control signals are transferred over a transcutaneous link by the headpiece coil via the implant coil to the stimulator device, which sends corresponding stimuli to appropriate electrodes of the electrode array that stimulate the recipient's auditory nerve to cause a perception of hearing.

Bilateral auditory systems include an auditory prosthesis fitted to both the right ear and left ear of a recipient. Each device in a bilateral system may operate independently of the other, or may communicate by either wireless or via a wired connection in delivering joint hearing assistance to the recipient.

One advantage of bilateral systems is the delivery of sound localization cues to a recipient. These cues include the difference in sound arrival time and/or the difference in sound intensity between the two ears.

There are challenges in delivering binaural cues to a recipient via bilateral auditory prostheses. In particular, processing gain varies from prosthesis to prosthesis. For example, louder sounds are suppressed more by automatic gain control (AGC) circuits in each prosthesis than softer sounds. As a result, a loud sound originating, for example, from the left side of a recipient is suppressed more by the left prosthesis than the right prosthesis, where due to head shadow it is received as a softer sound. As a result, the right AGC circuit may not suppress the louder sound at all or suppress it to a lesser extent. This may result in incorrect binaural cues being delivered (i.e. a delayed sound that has a louder or equivalent volume delivered to the right ear than the direct softer sound delivered to the left ear). This tends to adversely affect spatialisation capability, and may ultimately result in creating the impression that all sound is coming from the front.

In addressing these challenges, one approach is to synchronize the two prostheses in a bilateral system, such that the gain of certain events, such as electrical stimulation to auditory nerve fibers enacted by one prosthesis is controlled with respect to the gain in the other prosthesis.

Gain synchronization may be achieved by sending certain data across a communication channel between the two auditory prostheses in a bilateral system. The communication channel may be a wired connection, but in some prostheses the communication channel is an RF channel, such as a 2.4 GHz bidirectional RF channel.

A difficulty arises in using such a communications channel because presently such RF transceivers consume relatively large amounts of power, and this reduces the lifetime of the battery of an auditory prosthesis. Energy consumption may be reduced by operating the transceiver only intermittently or with a lower duty cycle. For example, packetized synchronization data may be sent for short time intervals, repeating every 64 milliseconds. However, the gap between successive synchronization data packets leads to a delay that can be unacceptably slow and incapable of delivering the correct binaural cues.

SUMMARY

In accordance with a first aspect of the present invention, there is provided a method for binaural synchronization between a first auditory prosthesis and a second auditory prosthesis of a bilateral auditory prosthesis system, the method comprising: receiving sound at least one of the first and second prostheses; detecting a synchronization trigger based on the sound; enabling a primary wireless communication channel between the first auditory prosthesis and the second auditory prosthesis in response to the synchronization trigger; and transferring synchronization data between the first and second auditory prostheses over the primary wireless communication channel.

In accordance with a second aspect of the present invention, there is provided a bilateral auditory prosthesis system comprising: a first auditory prosthesis and a second auditory prosthesis, each prosthesis including: at least one receiver configured to receive a sound signal;

a primary communications subsystem configured to communicate with the other auditory prosthesis via a primary communications channel; and a signal processor configured to process sound received at the at least one receiver to detect a synchronization trigger; wherein the first and second auditory prostheses are configured to enable a primary wireless communication channel between the first auditory prosthesis and the second auditory prosthesis in response to the detection of the synchronization trigger and transfer synchronization data between the first and second auditory prostheses over the primary wireless communication channel.

In accordance with a third aspect of the present invention, there is provided a bilateral auditory prosthesis system comprising a first auditory prosthesis and a second auditory prosthesis, the system comprising: means for receiving sound; means for detecting a synchronization trigger based on the sound; means for enabling a primary wireless communication channel between the first auditory prosthesis and the second auditory prosthesis in response to the synchronization trigger; and means for transferring synchronization data between the first and second auditory prostheses over the primary wireless communication channel.

BRIEF DESCRIPTION OF THE DRAWINGS

Illustrative embodiments of the present invention are described herein with reference to the accompanying drawings, in which.

DETAILED DESCRIPTION

Aspect of the present invention are generally directed to synchronization between a first auditory prosthesis and a second auditory prosthesis of a bilateral auditory prosthesis system. In this system, a primary wireless communications channel, usable for synchronizing the first and second prostheses, may be disabled to, for example, conserve power. Then, upon detection of a trigger in sound received by one or more of the prostheses, the primary wireless communication channel is enabled and the prostheses synchronized using the primary wireless communication channel.

Embodiments of the present invention are described herein primarily in connection with one type of hearing prosthesis, namely a cochlear prostheses (commonly referred to as cochlear prosthetic devices, cochlear implants, cochlear devices, and the like; simply "cochlea implants" herein.) Cochlear implants generally refer to hearing prostheses that deliver electrical stimulation to the cochlea of a recipient. As used herein, cochlear implants also include hearing prostheses that deliver electrical stimulation in combination with other types of stimulation, such as acoustic or mechanical stimulation (sometimes referred to as a hybrid device). It would be appreciated that embodiments of the present invention may be implemented in any cochlear implant or other hearing prosthesis now known or later developed, including auditory brain stimulators, or implantable hearing prostheses that acoustically and/or mechanically stimulate components of the recipient's middle or inner ear. It should be understood, however, embodiments of some aspects of the invention can also find application in bilateral auditory prosthesis system including an auditory prosthesis or prostheses other than a cochlear implant, such as for example, where one or more of the auditory prostheses is a bone conduction device, a direct acoustic cochlear stimulator, a hearing aid, etc. Therefore, aspects should not be considered as being limited to the field of application of the illustrative embodiments described herein.

Figure 1:
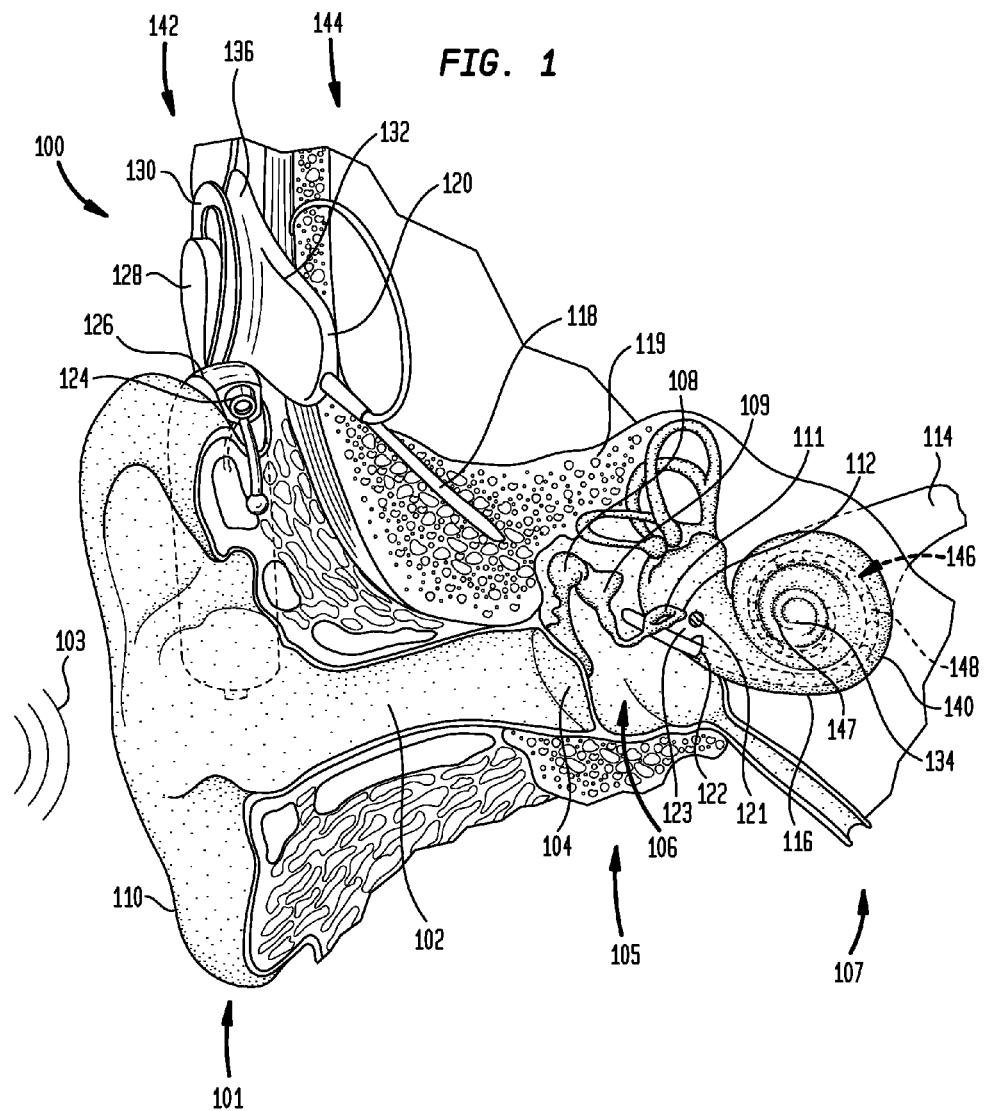
FIG. 1 is a perspective view of a cochlear implant for implant in a recipient, and which may be used in an embodiment of the present invention.

FIG. 1 is a perspective view of a cochlear implant 100, implanted in a recipient having an outer ear 101, a middle ear 105 and an inner ear 107. Components of outer ear 101, middle ear 105 and inner ear 107 are described below, followed by a description of cochlear implant system 100.

In a fully functional ear, outer ear 101 comprises an auricle 110 and an ear canal 102. An acoustic pressure or sound wave 103 is collected by auricle 110 and is channeled into and through ear canal 102. Disposed across the distal end of ear cannel 102 is the tympanic membrane 104 which vibrates in response to the sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 which is directly or indirectly attached to the body of the recipient, and an internal component 144 which is temporarily or permanently implanted in the recipient. External component 142 typically comprises one or more sound input elements, such as microphone 124 for detecting sound, a sound processing unit 126, a power source (not shown), and an external headpiece coil unit 128. External headpiece coil unit 128 comprises an external circular shaped coil 130 and, preferably, a magnet (not shown) secured directly or indirectly to external coil 130. Sound processing unit 126 processes the output of microphone 124 that is positioned, in the depicted embodiment, adjacent to the auricle 110 of the recipient. Sound processing unit 126 generates encoded signals, which are provided to the headpiece coil unit 128 via a cable (not shown).

Internal component 144 comprises internal receiver unit 132 including an implant coil 136, a stimulator unit 120, and an elongate electrode assembly 118. The internal receiver unit 132 may comprise a magnet (also not shown) fixed concentrically relative to the implant coil 136. The stimulator unit 120 is hermetically sealed within a biocompatible housing 132, sometimes collectively referred to as the implant unit. The implant coil 136 receives power and stimulation data from external coil 130, as noted above. Elongate electrode assembly 118 has a proximal end connected to stimulator unit 120, and a distal end implanted in cochlea 140. Electrode assembly 118 extends from stimulator unit 120 to cochlea 140 through the mastoid bone 119, and is implanted into cochlea 140. In some embodiments electrode assembly 118 may be implanted at least in basal region 116, and sometimes further. For example, electrode assembly 118 may extend towards apical end of cochlea 140, referred to as the cochlear apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises an electrode array 146 comprising a series of longitudinally aligned and distally extending electrodes 148, disposed along a length thereof. Although electrode array 146 may be disposed on electrode assembly 118, in most practical applications, electrode array 146 is integrated into electrode assembly 118. As such, electrode array 146 is referred to herein as being disposed in electrode assembly 118. Stimulator unit 120 generates stimulation signals which are applied by electrodes 148 to cochlea 140, thereby stimulating auditory nerve 114.

Because the cochlea is tonotopically mapped, that is, partitioned into regions each responsive to stimulus signals in a particular frequency range, each electrode of the implantable electrode array 146 delivers a stimulating signal to a particular region of the cochlea. In the conversion of sound to electrical stimulation, frequencies are allocated to individual electrodes of the electrode assembly that lie in positions in the cochlea that are close to the region that would naturally be stimulated in normal hearing. This enables the prosthetic hearing implant to bypass the hair cells in the cochlea to directly deliver electrical stimulation to auditory nerve fibers, thereby allowing the brain to perceive hearing sensations resembling natural hearing sensations. In achieving this, processing channels of the sound processing unit 126, that is, specific frequency bands with their associated signal processing paths, are mapped to a set of one or more electrodes to stimulate a desired nerve fiber or nerve region of the cochlea. Such sets of one or more electrodes for use in stimulation are referred to herein as "electrode channels" or "stimulation channels."

In cochlear implant 100, external coil 130 transmits electrical signals (i.e., power and stimulation data) to internal coil 136 via an inductive RF channel. Internal coil 136 is typically a closed loop wire antenna coil of multiple turns of electrically insulated single-strand or multi-strand platinum or gold wire. The electrical insulation of internal coil 136 is provided by a flexible silicone moulding (not shown). In use, implantable receiver unit 132 may be positioned in a recess of the temporal bone adjacent auricle 110 of the recipient.

As noted above, cochlear implant 100 of FIG. 1 may be used in bilateral implant systems. For example, in embodiments, a cochlear implant 100 may be fitted to both the right ear and left ear of a recipient to form a bilateral implant system. These cochlear implants in such a bilateral system may operate independently of one another, or may communicate by either wireless or via a wired connection in delivering joint stimulation to the recipient.

Figure 2:
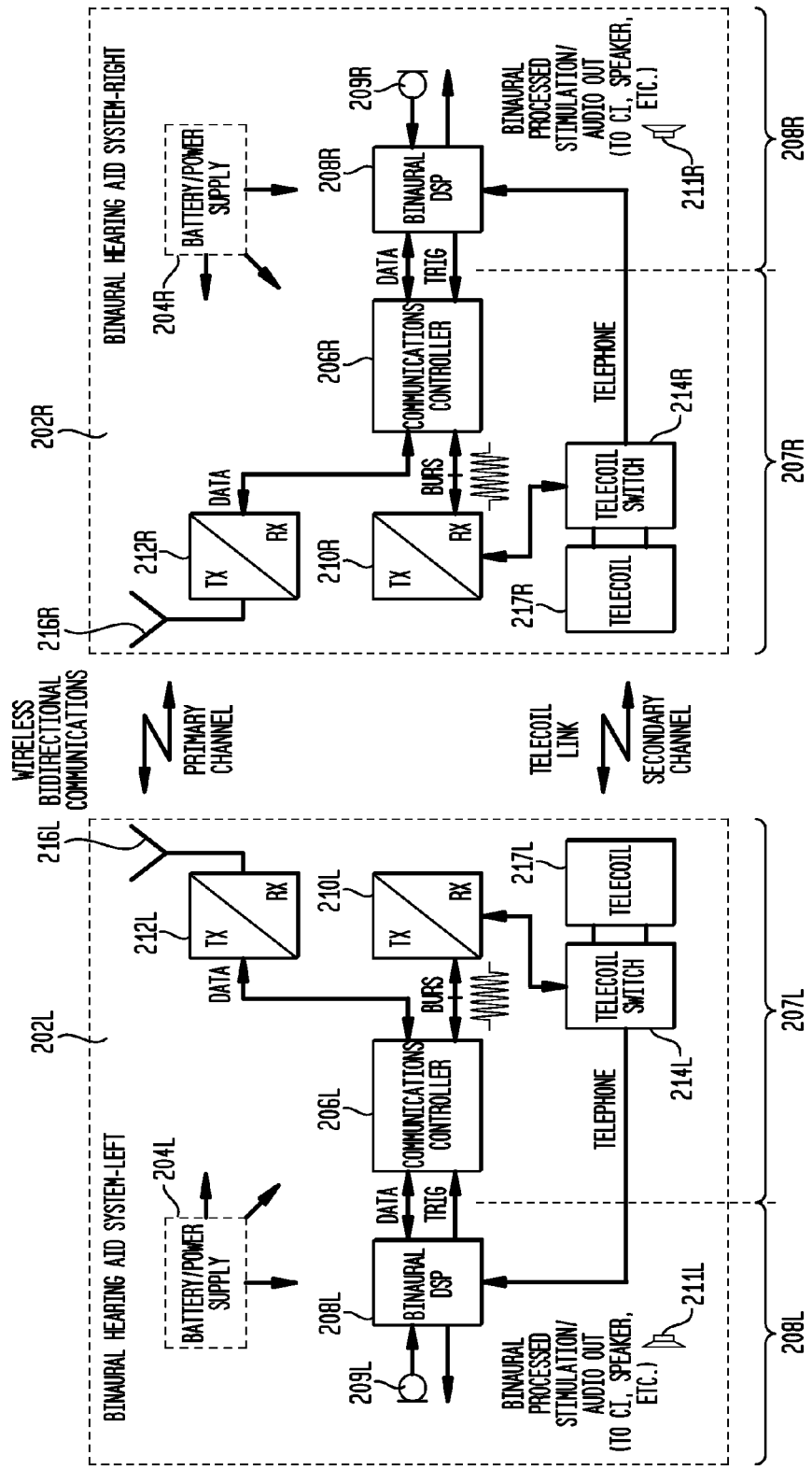
FIG. 2 is a schematic block diagram illustrating communications sub-systems of a left and right auditory prosthesis forming part of a bilateral auditory prosthesis system, in accordance with an embodiment of the present invention.

FIG. 2 is a block diagram of an exemplary bilateral implant system 200. FIG. 2 illustrates selected components of two auditory prostheses 202L and 202R used in forming a communications channel between the auditory prostheses. In the embodiment of FIG. 2, each of the auditory prostheses 202L and 202R may be a cochlear implant such as discussed above with reference to FIG. 1.

The bilateral auditory prosthesis includes a left auditory prosthesis 202L and a right auditory prosthesis 202R. The schematic block diagrams of the left prosthesis 202L and the right prosthesis 202R are substantially identical and accordingly related reference numerals will be used in describing each prosthesis. The reference numerals will differ by a suffix L or R to denote left and right side components which are equivalent.

Each auditory prosthesis 202L, 202R is part of the external component 142 of FIG. 1, which is connectable to the internal implant component 144. In an embodiment, one or more of the auditory prostheses may be a mostly implantable cochlear implant (MIKI) that includes both external and internal components substantially as described above. Or, for example, in an embodiment, one or more of the auditory prostheses may be a totally implantable cochlear implant (TIKI) in which all the external components described with reference to FIG. 1 are implanted internally.

As illustrated, each auditory prosthesis 202L, 202R includes the following subsystems:

A battery or power supply 204L, 204R for delivering power to the other components of its respective prosthesis 202L, 202R.

A communications controller 206L, 206R e.g. in the form of microprocessor, FPGA or other type of controller which controls the transceivers of each prosthesis.

A binaural digital signal processor 208L, 208R, which can also include interfaces to input and output systems e.g. one or more microphones 209L, 209R, one or more outputs, e.g. speakers 211L, 211R, a CI electrode array over headpiece coil channel (not shown), and/or data port(s) or other output devices.

A communications subsystem 207L, 207R includes a communications controller 206L, 206R which is in communication with a respective first transceiver 210L, 210R that is configured to transmit and receive using a secondary wireless communications channel, and a second transceiver 212L, 212R which is adapted to transmit and receive using a primary wireless communications channel. The secondary wireless communications channel is implemented as an inductive coupling between telecoils 217L, 217R. Each auditory prosthesis 202L, 202R includes a telecoil switch 214L, 214R. The telecoil switch 214L, 214R is used to select the manner in which received signals are routed through the device, e.g. directly to the binaural signal processor 208L, 208R or via communications controller 206L, 206R. The second transceiver 212L, 212R can be a radio frequency transceiver adapted to communicate wirelessly, for example at 2.4 GHz. The transceivers 212L, 212R are coupled to suitable antennas 216L, 216R.

The primary wireless communications channel is used for transmitting data between the left and right prostheses 202L, 202R. One type of data transmitted is synchronization data, for example automatic gain control (AGC) data which is used to co-ordinate the gains of the left and right prosthesis 202L, 202R to provide localization cues to the recipient of the binaural system 200. Conventionally, the secondary wireless channel, i.e. the telecoil channel, is used for providing external audio through a varying magnetic field to one or both of the auditory prosthesis 202L, 202R via an inductive loop from a telephone, assistive listening or other devices which are 'Hearing Aid Compatible' (HAC).

An embodiment of the present invention uses the telecoil channel to additionally transmit synchronization commencement signals between the left and right prosthesis device to enable synchronization to be performed rapidly if the devices are operating in an unsynchronized, or a poorly synchronized mode. This transmitted synchronization commencement signal may be a low frequency burst signal, e.g., a 4 KHz signal, placed on the telecoil, but can also be a multi-tone carrier, chirp or frequency-swept signal. Or, for example, the synchronization commencement signal may be a signal including data, such as a message, or any other type useful in enabling the establishment of a communication between the prostheses. The process for commencing synchronization in this fashion is described in more detail below in connection with FIGS. 3 and 4.

Telephone detector and mute settings can also be communicated between the auditory prostheses over the wireless telecoil channel via, for example, a 10 KHz signal, and serial numbers may additionally be transferred over the telecoil channel at a very low data rate.

Because the secondary wireless communications channel is implemented using a telecoil, the secondary wireless communications channel may be permanently active when the two devices 202L and 202R are sufficiently close to each other for inductive coupling between the telecoil loops of each device to automatically occur, which typically corresponds to the approximate 20 cm in situ distance between the left and right auditory prostheses. Advantageously, this form of communication uses little battery power and has a negligible affect on battery life.

When the primary wireless communications channel is active, high power consumption may occur, which may quickly drain the battery. Accordingly, if the primary wireless communications channel can be fully or partially deactivated, the system may conserve battery power. In order to conserve power, in an embodiment, the two auditory prostheses 202L and 202R operate in a low synchronization mode in which the auditory prostheses 202L and 202R are only periodically synchronized or at least allowed to remain unsynchronized for extended periods. Thus, the primary wireless communication channel, which is used for transmitting synchronization data, can be deactivated for periods of time thus conserving battery power.

Figure 3:
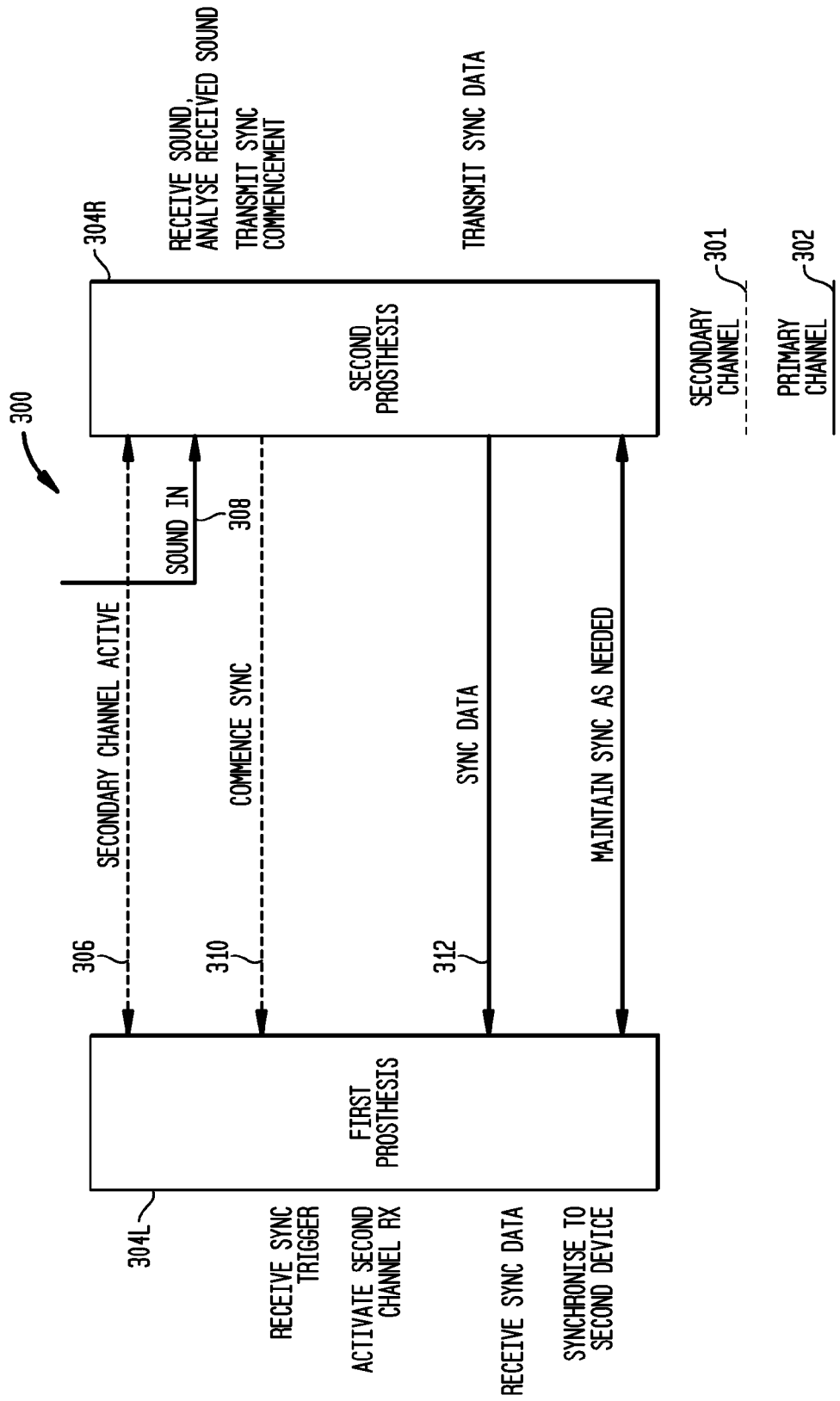
FIG. 3 illustrates a flow diagram of a method for a low synchronization mode, in accordance with an embodiment of the present invention.

FIG. 3 illustrates a communications method 300 for a low synchronization mode of communications between a first auditory prosthesis 304L and a second auditory prosthesis 304R. As noted above, auditory prostheses 304L and 304R may communicate over a wireless secondary communications channel, indicated by dotted lines 301, and a primary wireless communications channel 302, indicated by solid lines 302. Initially, the primary wireless communications channel 302 is inactive and the secondary wireless channel 306 is active. Next, an auditory input 308 is received and evaluated by the second auditory prosthesis 304R.

The second auditory prosthesis 304R analyzes the received sound to determine if a synchronization trigger has occurred. In the present embodiment, a synchronization trigger is deemed to occur if the received sound is determined to meet a specified criteria (or criterion). For example, in the present embodiment, secondary auditory prosthesis 304R may analyze the sound to determine whether the sound meets certain criteria for reactivating (or activating) synchronization between the left and right prostheses. If the criteria is met, the system may activate the primary wireless communication channel and synchronize the first and second auditory prostheses.

In embodiments, the synchronization criteria might be based on the sound level (e.g., in terms of dB) of the received sound or sound energy of the received sound over a specified time period. This sound level and/or energy may be the sound level or energy over certain frequency bands or the entire frequency range of the received sound. Or, for example, the rate of change of the sound level or energy may be used as a criteria for determining whether the sound includes a synchronization trigger to reactivate synchronization between the left and right prostheses. In other embodiments, the criteria may be based on more complex algorithms, such as algorithms that compare the variation of the fast-AGC level to a threshold or check the rate of change of the AGC against a threshold. A fast-AGC normally has a time constant of 1 ms. In practice the AGC is calculated using an FFT over 5 ms so only big variations may be expected every 5 ms, within the result that the AGC time constant becomes virtually slower.

When the synchronization criteria is met (i.e., the sound includes a synchronization trigger), the second auditory prosthesis 304R transmits a synchronization commencement signal 310 using the secondary wireless communications channel. The synchronization commencement signal 310 can be implemented as a short chirp e.g. at 4 kilohertz, applied on the telecoil. This may generate a non audible magnetic field which couples with the telecoil of the left device 304L. Alternatively, if the telecoil excitation frequency is higher the commence synchronization transmission signal 310 can be used to encode some data.

The first auditory prosthesis 304L receives the synchronization commencement signal 310, and thus determines that a synchronization trigger has occurred. In response, the first auditory prosthesis 304L activates its receiver to enable reception on the primary communication channel. Next, the second auditory prosthesis 304R transmits synchronization data 312, which may be packaged in a message (referred to as a synchronization message) over the primary wireless channel, which is received by the first auditory prosthesis 304L. The first auditory prosthesis 304L then uses this data to synchronize itself with the second auditory prosthesis 304R. In certain implementations of the present invention, the first auditory prosthesis 304L and second auditory prosthesis 304R may exchange additional transmissions on the primary wireless communications channel in order to establish or maintain synchronization. Typically, the first synchronization data transmitted will include fast automatic gain control data, e.g. bytes of AGC data. This allows synchronization to take place extremely quickly e.g. within one millisecond of the sound 308 being received. The AGC level can be expressed in dB (in a number from 0 to 127) when transmitted over the primary wireless channel.

Ongoing synchronization between the first and second prostheses 304L and 304R can be maintained using the primary wireless communications channel until it is deemed to be no longer required. After which, the primary wireless communications channel may be deactivated.

Figure 4:
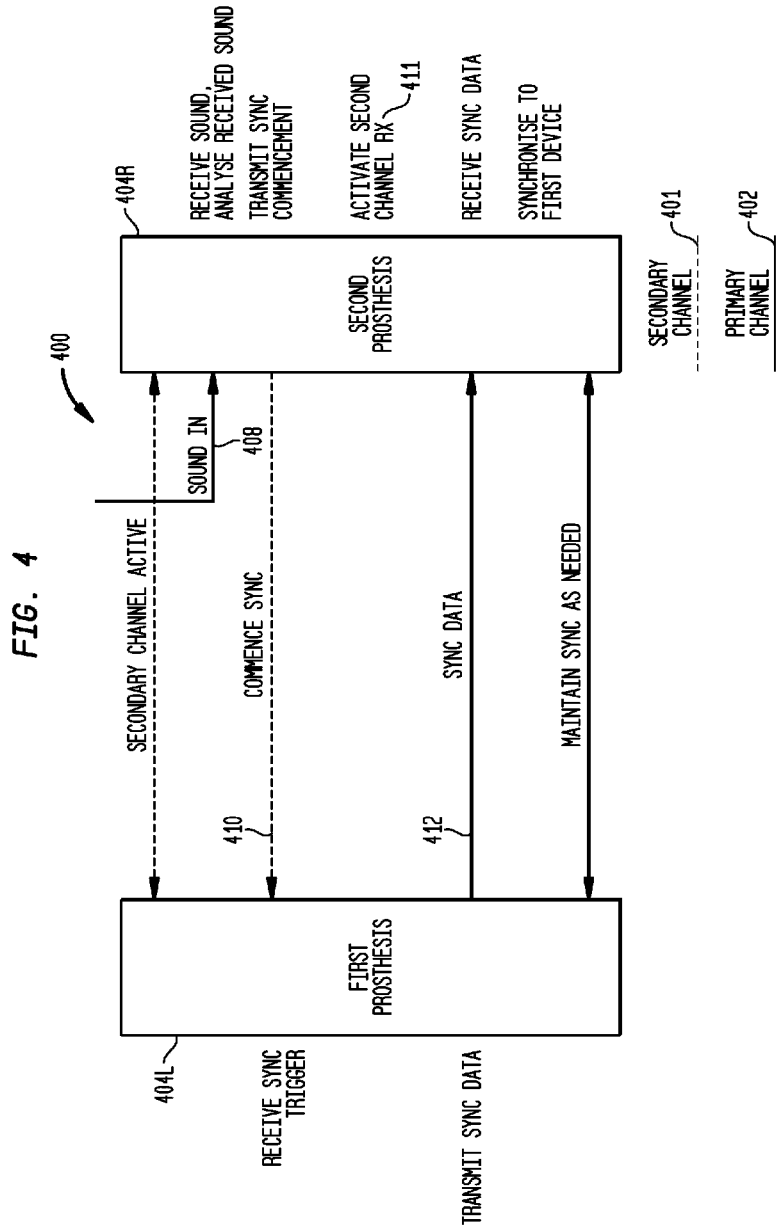
FIG. 4 illustrates a flow diagram of another method for a low synchronization mode, in accordance with an embodiment of the present invention.

FIG. 4 shows an alternative method, in which some of the roles in the process are reversed between the first and second auditory prosthesis. In FIG. 4, communications over the secondary wireless communications channel are illustrated by dotted lines 401 and communications over the primary wireless communications channel are indicated by solid lines 402. In this example, the secondary wireless communications channel is a telecoil channel and the primary wireless communications channel is an RF channel, such as discussed above with reference to FIG. 2.

In this example, the first and second prostheses 404L and 404R are operating in a state where they are substantially unsynchronized and the secondary wireless communications channel 406 is initially active. Next a sound 408 is received. As before, the second auditory prosthesis 404R receives the sound, performs an analysis to determine whether the sound includes a synchronization trigger (i.e., the sound when analyzed is determined to meet a specified criteria or criterion) and, if so, commences synchronization. In the event that synchronization is deemed necessary (i.e., sound includes a synchronization trigger), the second auditory prosthesis 404R transmits a commence synchronization signal 410 to the first auditory prosthesis 404L over the secondary communications channel. The second auditory prosthesis 404R also activates its receiver for the primary wireless communications channel, indicated as step 411. Upon receipt of the synchronization commencement signal 410, the first auditory prosthesis 404L determines that a synchronization trigger has occurred and transmits synchronization data 412 back to the second auditory prosthesis 404R. This synchronization data 412 may include data similar to the synchronization data 312 discussed above. The first auditory prosthesis 404L also can activate its receiver for the primary wireless communications channel and if additional synchronization data is to be exchanged between the first and second auditory prosthesis 404L and 404R. Additional synchronization messages are transmitted between the prostheses using the primary wireless communications channel 402. When synchronization is no longer needed synchronization communications via the primary wireless communications channel 402 can be terminated.

Figure 5:
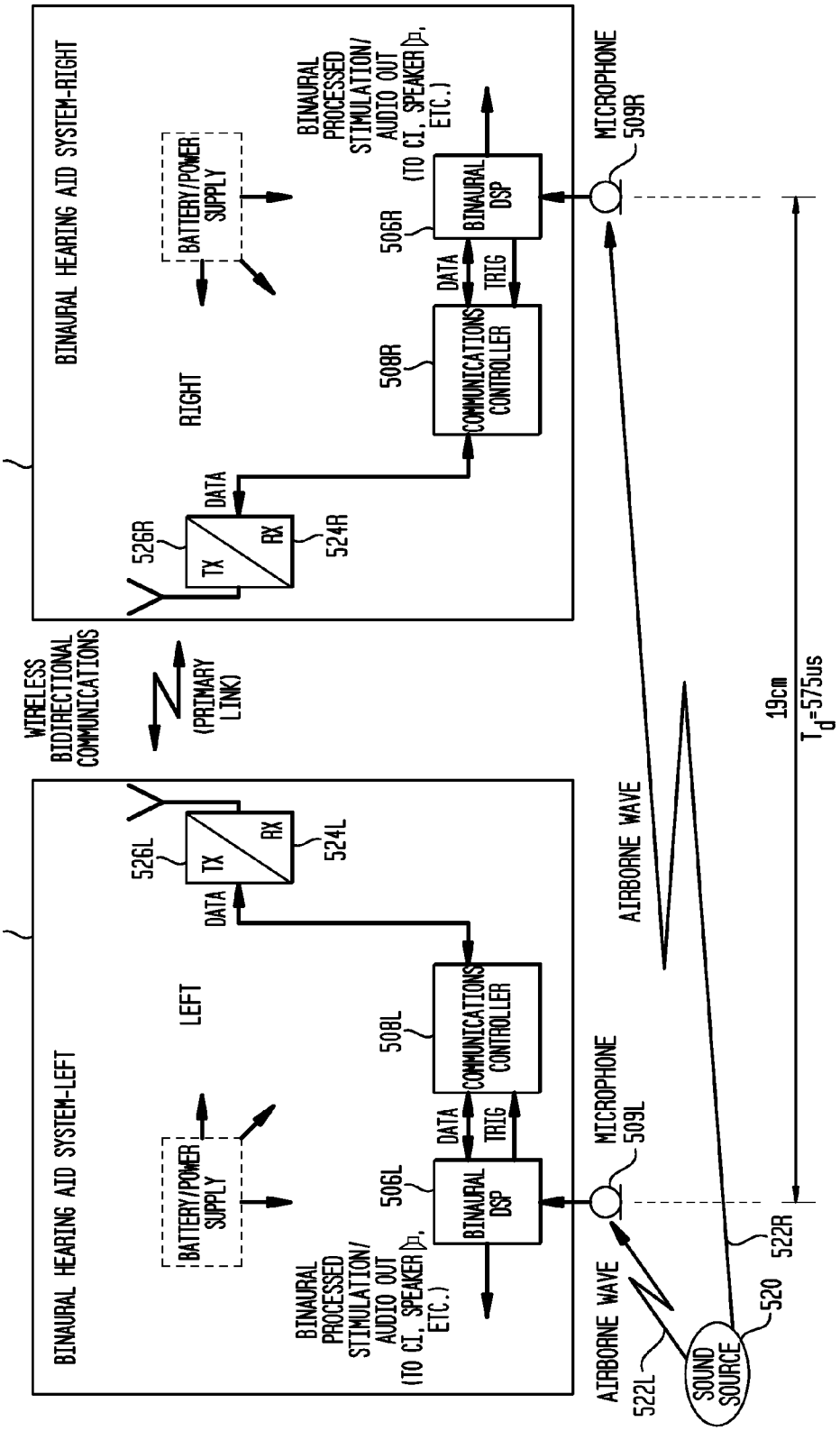
FIG. 5 is a schematic block diagram illustrating communications sub-systems of a further embodiment of left and right auditory prostheses, in accordance with an embodiment of the present invention.

FIG. 5 illustrates another embodiment of a bilateral auditory prosthesis system. In the embodiment of FIG. 5, the bilateral system includes left and right prostheses 502L and 502R similar to those indicated in FIG. 2. Similar components are identified with the same numbers prefixed by a "5" rather than a "2". The main difference is that a telecoil channel is no longer used, together with all the components required to communicate via a telecoil, including the telecoil, the telecoil switch and the first transceiver. Instead, a sound source 520 (offset to the left of FIG. 5) generates an airborne wave comprising components 522L and 522R that are sensed at the respective microphones 509L and 509R of the auditory prostheses 502L and 502R. In this example the prostheses 502L and 502R directly determine whether the sound components include a synchronization trigger independently of each other on the basis of the received sound. In this embodiment, the prostheses 502L and 502R need not communicate via a secondary wireless communications channel to initiate synchronization. The prostheses 502L and 502R may determine that the sound includes a synchronization trigger by analyzing the sound to determine whether sound meets a specified criteria or criterion as discussed above.

The microphones 509L and 509R are typically spaced about 19 cm apart on either side of the head, with the result that in the case of the sound source 520 originating directly from the left, the $T_d$ between the microphone 509L picking up the sound wave component 522L and the microphone 509R picking up the sound component 522R is approximately 575 μs.

Figure 6:
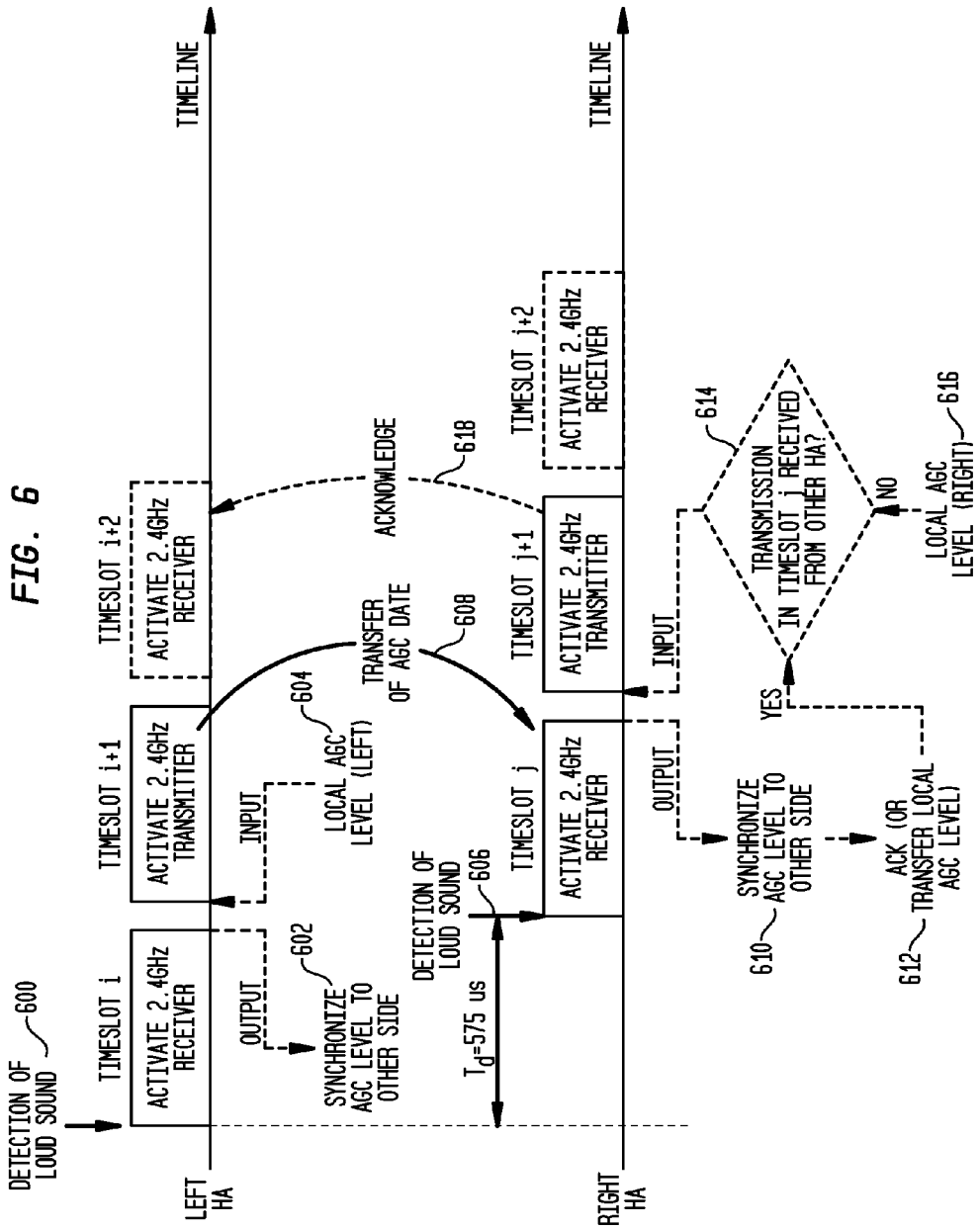
FIG. 6 is a timing diagram for synchronization of the system of FIG. 5 in the event of a sound including a synchronization trigger, in accordance with an embodiment of the present invention.

FIG. 6 illustrates an exemplary timing diagram, in accordance with an embodiment of the present invention. FIG. 6 will be described with reference to FIG. 5 to explain an exemplary method for a low synchronization mode of operation. As illustrated, the method is initiated by the detection of a synchronization trigger in the received sound. In this example, the sound is deemed to include a synchronization trigger if the sound is loud sound 600 (e.g., the analyzed sound is determined to have an amplitude greater than a specified amplitude) at the microphone 509L. In response, the 2.4 GHz receiver 524L is activated in time slot i. The receiver then listens for (and synchronizes if detected) synchronization data (which in this example is an AGC level signal from the right auditory prosthesis 502R) as is shown by arrow 602, in the event of the right transmitter being activated first. At the commencement of time slot i+1, the 2.4 GHz transmitter 526L is activated, and is provided with an input generated at an AGC circuit forming part of the left DSP 506L via the communications controller 508L. The gain level of the left AGC circuit is reduced in response to the receipt of the loud sound at the microphone 509L. The left HA 5002L then transmits this gain level (i.e., synchronization data) via the 2.4 GHz transmitter, as shown by arrow 604. Thus, in this exemplary, the synchronization commencement message is the initial signal transmitted from one of the prostheses that includes synchronization data. As noted above, this synchronization data may be packaged in a synchronization message.

Meanwhile, at the right auditory hearing aid (HA) prosthesis 502R, the loud sound component 522R is detected at the microphone 509R after a time delay of 575 μs. In response to this synchronization trigger, the 2.4 GHz receiver 524R is activated in time slot j. The time slot j overlaps with the time slot i+1, and as a result AGC data can be transferred from the transmitter 526L to the receiver 524R, as is shown at 608.

It will be appreciated that the largest time slot duration $T_d$ is for sound sources located at a localization angle Ø of about 0° which corresponds to the sound wave approaching directly from the left or the right of the microphones. As the localization angle increases, $T_d$ decreases, and therefore varies from 575-407 μs for angles between 0-45°. In this exemplary embodiment, data can only be transferred when the Tx and Rx slots overlap with each other, as is shown in the case of time slot i+1 and time slot j. As the AGC information is small (1 byte) and transmissions can occur at high symbol rates (i.e. 300 kbps to 1 Mbps), retransmission (also referred to as retrials) during the same timeslot can occur. Such retrials could enable AGC data to successfully be transferred in the case of partially overlapping timeslots.

Once transferred at 608 during the timeslot j, the AGC data is transmitted from the receiver 525R via the communications controller 508R to the DSP 506R. The AGC data which originated at the left DSP 506L is applied to the AGC of the right DSP 506R, with the result that the AGC levels in both the left and right prostheses are effectively synchronized and equalized, as is shown at 610. The right transmitter 526R is activated at timeslot j+1 and receives as an input an acknowledge signal, as is shown at 612, acknowledging synchronization of the AGC level at 610. The acknowledge signal is then transmitted back to the receiver 524L, as is shown at 618.

Alternatively, as is shown at 614, in the event of a transmission not being received from the other (left) hearing aid prosthesis 502L, the local AGC level from the right DSP 506R is applied to the transmitter 526R at the commencement of timeslot j+1. This would typically occur in the event of the sound source 520 emanating from the right rather than the left, the opposite of the example described and illustrated in full in FIGS. 5 and 6.

Figure 7:
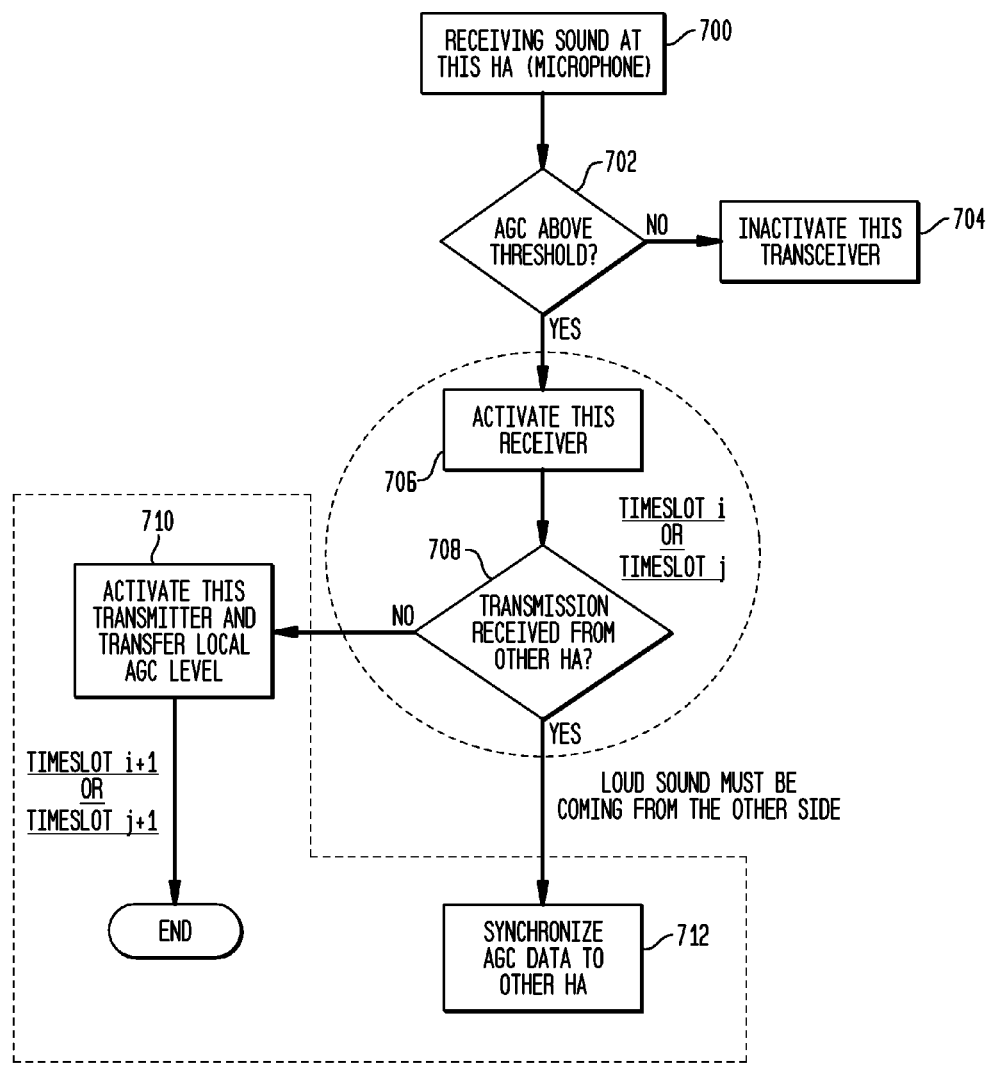
FIG. 7 is a flowchart applicable to auditory prosthesis of FIG. 5, in accordance with an embodiment of the present invention.

FIG. 7 is a flowchart of an exemplary synchronization process, in accordance with an embodiment of the present invention. As illustrated, the synchronization process commences at 700 with the sound being received at one of the microphones 509L or 509R. In the event of the received sound not being above the threshold to which the AGC is set, at 702, the relevant transceiver is deactivated or remains inactive at 704. In other words, a synchronization trigger is not detected.

In the event of the sound being above the AGC threshold, and thus a synchronization trigger occurring, the relevant local receiver is activated at 706, and the auditory prosthesis checks at 708, during timeslot i or timeslot j, whether a transmission has been received from the other auditory prosthesis. If not, the local transmitter is activated at 710 and the local AGC level is transmitted during timeslot i+1 or timeslot j+1 to the other receiver to ensure that the AGC level is synchronized and applied uniformly to the right and left auditory prostheses. In the event of the transmission being received from the other auditory prosthesis, it is concluded that the loud sound must be coming from the other side, and the AGC data from this other side is then applied and synchronized with the auditory prosthesis referred to at 712. In FIG. 7, the steps enclosed by the dotted line indicate receiving steps performed by the auditory prosthesis (e.g., activating the receiver and checking whether a transmission was received). The steps enclosed by the solid line indicate steps involving transmission of information (e.g., activating the transmitter, transmitting AGC level, and communicating with the other auditory prosthesis for synchronization purposes).

Figure 8:
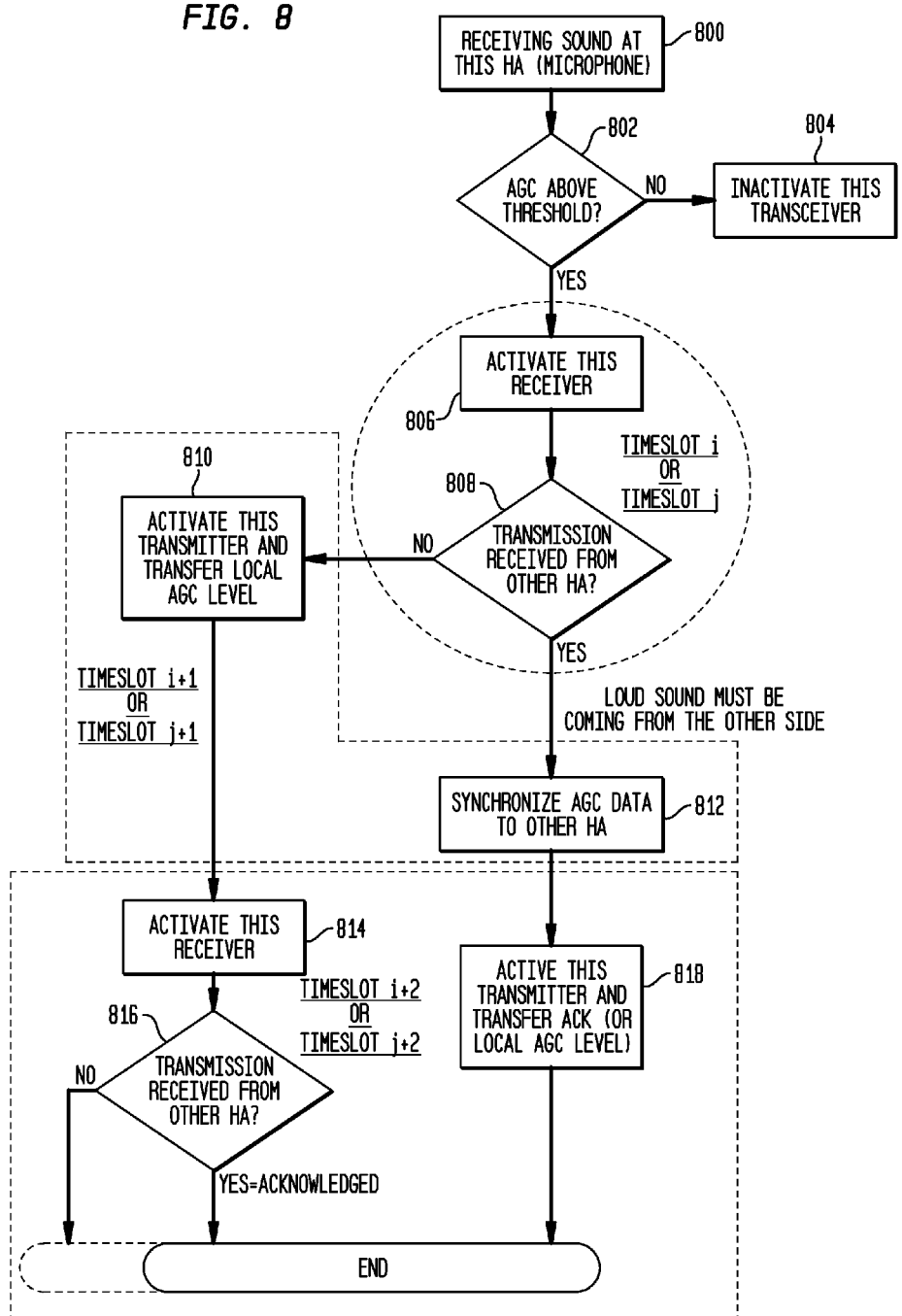
FIG. 8 is an extended flowchart of the flowchart of FIG. 8, in accordance with an embodiment of the present invention.

FIG. 8 shows an extended process flowchart, the first part of which is identical to the flowchart of FIG. 7, with corresponding steps being prefixed by an 8 rather than a 7. The subsequent steps illustrated in FIG. 8 (and enclosed by the solid line at the bottom of FIG. 8) also correspond largely to the steps referred to in the timing diagram of FIG. 6. In particular, the receiver is activated, for example, during timeslot i+2 or j+2e. At decision diamond 816, once the transmission has been received from the other auditory prosthesis or HA, the auditory prosthesis transmits an acknowledgment. If a transmission is not received, the local AGC level used by the auditory prosthesis in processing the received sound.

Proceeding from step 812, after the AGC data has been synchronized with that of the other auditory/HA prosthesis, the local transmitter is activated and transfers an acknowledge signal (or a local AGC level as the case may be) at step 818. This is shown as step 618 in FIG. 6.

It will be appreciated that the synchronization and equalization process described above ensures that as a general rule, the gain control of the binaural system is governed by the gain control of the first AGC to respond to the incoming sound. As a result, gain control compensation is equalized for both left and right prostheses, regardless of the later arriving sound level. This means that the local AGC associated with the later arriving sound level does not under-compensate by reducing the softer sound less, which would result in the true sound levels not be accurately replicated, and the recipient receiving the later arriving sound with the same or possibly even a greater volume than the earlier arriving naturally louder sound.

As can be seen from the foregoing embodiments, implementations of the present invention enable rapid synchronization of left and right prosthesis of a bilateral auditory prosthesis system which can advantageously provide localization cues to the recipient of the system. Additionally, by reusing telecoils already provided in conventional auditory prosthesis, or by not relying on telecoils in the first place, no additional hardware is required.

It is also possible to adapt the system for use with other types of transmission channel to perform the role of the first and/or second communications channel. For example, instead of the telecoil transmission system, each prosthesis could be provided with transducers for transmitting and or receiving, electromagnetic, optical or ultrasonic signals. Preferably the transmission system for the secondary wireless communications channel is connected to a low power amplifier comparator which operates with a much lower power consumption than the primary wireless communications channel. Whilst not as preferable as reusing the existing telecoil system or relying only on the existing 2.4 GHz radio channel, such implementations may be practical in some devices. Additionally, audio signals, optical signals or other EM radiation bands could be used for either or both of the first or second transmission channels.

It will be understood that the invention disclosed and defined in this specification extends to all alternative combinations of two or more of the individual features mentioned or evident from the text or drawings. All of these different combinations constitute various alternative aspects of the invention.

What is claimed is:

1. A method for binaural synchronization between a first auditory prosthesis and a second auditory prosthesis of a bilateral auditory prosthesis system, the method comprising:
receiving sound at one or more of the first and second prostheses;
analyzing the received sound at one of the first and second auditory prostheses;
detecting a synchronization trigger if at least one predetermined criterion is met by the analyzed sound, wherein detecting the synchronization trigger includes at least one of: (i) determining that a sound level of the received sound exceeds a threshold, (ii) determining that an energy level of the received sound exceeds a threshold, (iii) determining that a rate of change of the sound level exceeds a threshold, (iv) determining that a rate of change of the energy level exceeds a threshold, (v) determining that an automatic gain control level determined in analyzing the sound exceeds a threshold, and (vi) determining that a rate of change of an automatic gain control level determined in analyzing the sound exceeds a threshold;
enabling a primary wireless communication channel between the first auditory prosthesis and the second auditory prosthesis in response to the synchronization trigger; and
transferring synchronization data between the first and second auditory prostheses over the primary wireless communication channel.

2. The method of claim 1, further comprising:
transmitting a synchronization commencement signal from the one of the first or second auditory prostheses to the other of the first or second auditory prostheses via a secondary wireless communication channel.

3. The method of claim 1, further comprising:
operating the first and second auditory prostheses in a first state in which the primary wireless communication channel is at least partially disabled.

4. The method of claim 3, wherein the secondary wireless communication channel is enabled at least during a period when the first and second auditory prostheses are in the first state.

5. The method of claim 3, wherein the secondary wireless communication channel is permanently enabled.

6. The method of claim 1, wherein transferring synchronization data between the first and second auditory prostheses over the primary wireless communication channel comprises:
transferring gain control data to coordinate gain control applied by each auditory prosthesis.

7. The method of claim 1 wherein the synchronization data comprises gain control data, and wherein said method further comprises:
applying the gain control data to the other auditory prosthesis.

8. The method of claim 1 wherein enabling a primary wireless communication channel between the first auditory prosthesis and the second auditory prosthesis comprises:
activating a receiver of a prosthesis of the first and second prostheses at which the synchronization trigger is detected, wherein said receiver is configured to receive transmissions on the primary wireless communications channel; and
listening via the activated receiver for a transmission including synchronization data from the other auditory prosthesis on the primary transmission channel.

9. The method of claim 8 wherein the synchronization data comprises gain control data, and wherein, in the event of the synchronization data being received at the activated receiver, the method further comprising:
applying said gain control data to the auditory prosthesis associated with the activated receiver to synchronize the auditory prostheses.

10. The method of claim 8 wherein, in the event of synchronization data not being received within a time period via the activated receiver after detecting the synchronization trigger, the method further comprises:
activating a transmitter of the prosthesis at which the synchronization trigger was detected; and transmitting synchronization data to the other auditory prosthesis on the primary transmission channel.

11. The method of claim 10, further comprising:
receiving the synchronization data at the other auditory prosthesis; and
using said synchronization data to synchronize the other auditory prosthesis with the auditory prosthesis at which the synchronization trigger was detected.

12. A bilateral auditory prosthesis system comprising:
a first auditory prosthesis and a second auditory prosthesis, each prosthesis including:
at least one receiver configured to receive a sound signal;
a primary communications subsystem configured to communicate with the other auditory prosthesis via a primary communications channel; and
a signal processor configured to process sound received at the at least one receiver to detect a synchronization trigger;
wherein the first and second auditory prostheses are configured to enable a primary wireless communication channel between the first auditory prosthesis and the second auditory prosthesis in response to the detection of the synchronization trigger and transfer synchronization data between the first and second auditory prostheses over the primary wireless communication channel,
wherein in enabling the primary wireless communication channel, each of the first and second prostheses are configured to operate: in a first state in which the primary communications subsystem is at least partially disabled; and in a second state in which the primary communications subsystem is enabled to allow exchange of synchronization data over the primary wireless communication channel, and
wherein the signal processor of each of the first and second auditory prostheses is configured to cause the prosthesis to move from operating in the first state to the second state upon detection of the synchronization trigger in the processed sound.

13. The bilateral auditory prosthesis system of claim 12 wherein each of the first auditory prosthesis and the second auditory prosthesis further comprise:
a secondary communications subsystem configured to communicate with the other auditory prosthesis via a secondary communications channel.

14. The bilateral auditory prosthesis system of claim 13 wherein the secondary communications subsystem of each of the first and second auditory prostheses is configured to be enabled when the prosthesis is in a state in which the primary wireless communications channel is at least partially disabled.

15. The bilateral auditory prosthesis system of claim 12 wherein power consumption by the secondary communications subsystem is less than power consumption by the primary communication subsystem in the enabled state.

16. A method for binaural synchronization between a first auditory prosthesis and a second auditory prosthesis of a bilateral auditory prosthesis system, the method comprising:
receiving sound at one or more of the first and second prostheses;
detecting a synchronization trigger based on the sound; and
enabling a primary wireless communication channel between the first auditory prosthesis and the second auditory prosthesis, which comprises:
analyzing the received sound at one of the first and second auditory prostheses;
detecting a synchronization trigger if at least one predetermined criterion is met by the analyzed sound;
transmitting a synchronization commencement signal from the one of the first and second auditory prostheses; and
receiving the synchronization commencement signal at the other of the first and second auditory prostheses.

17. The method of claim 16, further comprising:
transmitting the synchronization commencement signal from the one of the first or second auditory prostheses to the other of the first or second auditory prostheses via a secondary wireless communication channel.

18. The method of claim 16 wherein detecting the synchronization trigger if at least one predetermined criterion is met comprises at least one of:
determining that a sound level of the received sound exceeds a threshold;
determining that an energy level of the received sound exceeds a threshold;
determining that a rate of change of the sound level exceeds a threshold;
determining that a rate of change of the energy level exceeds a threshold;
determining that an automatic gain control level determined in analyzing the sound exceeds a threshold; and
determining that a rate of change of an automatic gain control level determined in analyzing the sound exceeds a threshold.

19. The method of claim 16 wherein enabling a primary wireless communication channel comprises:
activating a receiver of at least one of the first or second auditory prostheses to receive transmission on the primary wireless communications channel, in response to receiving the synchronization commencement signal on the secondary wireless communications channel.

20. The method of claim 19 wherein enabling the primary wireless communication channel further comprises:
activating a transmitter of said one of the first or second auditory prostheses.

21. A method for binaural synchronization between a first auditory prosthesis and a second auditory prosthesis of a bilateral auditory prosthesis system, the method comprising:
receiving sound at one or more of the first and second prostheses;
detecting a synchronization trigger based on the sound;
enabling a primary wireless communication channel between the first auditory prosthesis and the second auditory prosthesis in response to the synchronization trigger, wherein enabling the primary wireless channel includes:
activating a receiver of a prosthesis of the first and second prostheses at which the synchronization trigger is detected, wherein said receiver is configured to receive transmissions on the primary wireless communications channel, and
listening via the activated receiver for a transmission including synchronization data from the other auditory prosthesis on the primary transmission channel; and
transferring synchronization data between the first and second auditory prostheses over the primary wireless communication channel.

* * * * *